(12) United States Patent
Bostrom

(10) Patent No.: US 8,892,373 B2
(45) Date of Patent: Nov. 18, 2014

(54) METHOD FOR DETERMINING THE STARTING INSTANT OF A PERIODICALLY OSCILLATING SIGNAL RESPONSE

(75) Inventor: Jan Bostrom, Gothenburg (SE)

(73) Assignee: Axsensor AB, Gothenburg (SE)

(*) Notice: Subject to any disclaimer, the term of this patent is extended or adjusted under 35 U.S.C. 154(b) by 632 days.

(21) Appl. No.: 12/998,489

(22) PCT Filed: Oct. 23, 2009

(86) PCT No.: PCT/EP2009/063992
§ 371 (c)(1),
(2), (4) Date: Jul. 7, 2011

(87) PCT Pub. No.: WO2010/049363
PCT Pub. Date: May 6, 2010

(65) Prior Publication Data
US 2011/0264387 A1  Oct. 27, 2011

(30) Foreign Application Priority Data
Oct. 28, 2008  (EP) .................................. 08167726

(51) Int. Cl.
*G01N 29/00*  (2006.01)
(Continued)

(52) U.S. Cl.
CPC .... *G01N 29/024* (2013.01); *G01N 2291/02836* (2013.01); *G01N 29/48* (2013.01);
(Continued)

(58) Field of Classification Search
CPC . G01N 29/024; G01N 29/44; G01N 29/4427; G01N 29/4454; G01N 29/48; G01H 5/00; G01F 1/66; G01F 1/666

USPC ............................................................. 702/56
See application file for complete search history.

(56) References Cited

U.S. PATENT DOCUMENTS 4,933,915 A * 6/1990 Bostrom .......................... 367/99
6,226,598 B1   5/2001 De Vanssay et al.
(Continued)

FOREIGN PATENT DOCUMENTS

DE      10106308 C1   7/2002
EP       1111349 A1   6/2001
(Continued)

OTHER PUBLICATIONS

Japanese Office Action dated Aug. 27, 2013 issued in corresponding Japanese Appln. No. 2011-532647.

*Primary Examiner* — Mischita Henson
*Assistant Examiner* — Terence Stifter, Jr.
(74) *Attorney, Agent, or Firm* — Harness, Dickey & Pierce, P.L.C.

(57) ABSTRACT

A method for determining the starting instant ($t_0$) of a periodically oscillating signal response (E2; E2'), wherein the signal response comprises a first set of half periods (E2a-d; E2'a-d) having a polarity equal to a polarity of the first half period (E2a; E2'a) in the signal response, and a second set of half periods (E2e-h; E2'e-h) having a polarity opposite to the polarity of the first half period (E2a; E2'a) in the signal response.

The method comprises the steps of: determining a peak half period (E2e; E2'f) as the half period with the highest amplitude in a selected one of the first and second sets; determining a zero-crossing instant (ZC1; ZC'1) of the signal response occurring a known time distance from the peak half period (E2e; E2'f); determining the starting instant ($t_0$) of the signal response (E2; E2') based on the zero-crossing instant (ZC1; ZC'1) and a relationship between the peak half period (E2e; E2'f) and the starting instant ($t_0$).

16 Claims, 6 Drawing Sheets

(51) Int. Cl.

| | | |
|---|---|---|
| *G01N 29/44* | (2006.01) | |
| *G01N 29/36* | (2006.01) | |
| *G01N 29/38* | (2006.01) | |
| *G01H 5/00* | (2006.01) | |
| *G01F 1/66* | (2006.01) | |
| *G01N 29/024* | (2006.01) | |
| *G01N 29/48* | (2006.01) | |
| *G01F 23/296* | (2006.01) | |

(52) U.S. Cl.
CPC ........ *G01N 29/4454* (2013.01); *G01F 23/2962* (2013.01)
USPC .... 702/56; 73/861.17; 73/861.18; 73/861.19; 73/861.23; 73/861.24; 73/861.25; 73/861.26; 73/861.27; 702/54; 702/48; 702/50; 702/55

(56) References Cited

U.S. PATENT DOCUMENTS

| | | |
|---|---|---|
| 2002/0011119 A1 | 1/2002 | Bignell et al. |
| 2004/0107774 A1 | 6/2004 | Arndt |
| 2007/0186624 A1 | 8/2007 | Koerdt et al. |
| 2007/0186680 A1* | 8/2007 | Lang .................. 73/861.27 |

FOREIGN PATENT DOCUMENTS

| | | |
|---|---|---|
| JP | 08-254454 | 10/1996 |
| JP | 10-186060 | 7/1998 |
| JP | 2004-163138 | 6/2004 |
| JP | 2005-049302 | 2/2005 |
| JP | 2006-275608 | 10/2006 |
| JP | 2007-243656 | 9/2007 |
| JP | 2008-190971 | 8/2008 |
| WO | WO-02071091 A2 | 9/2002 |

* cited by examiner

Fig. 2a
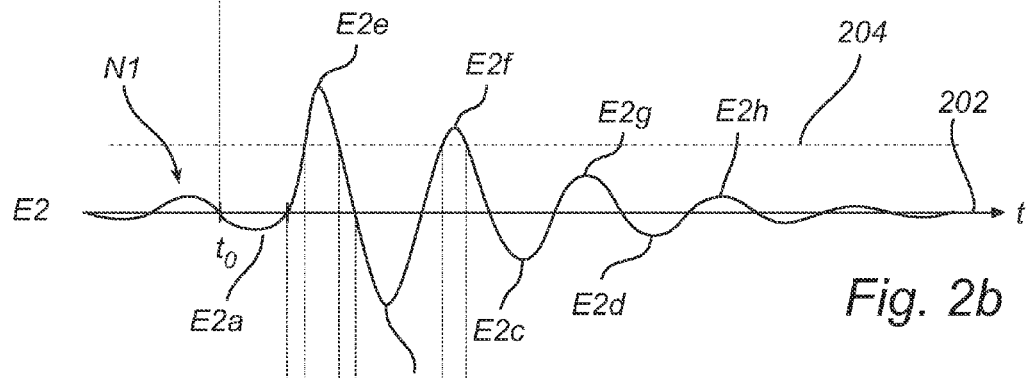
Fig. 2b
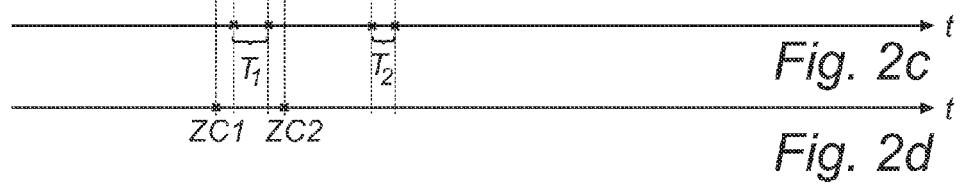
Fig. 2c
Fig. 2d
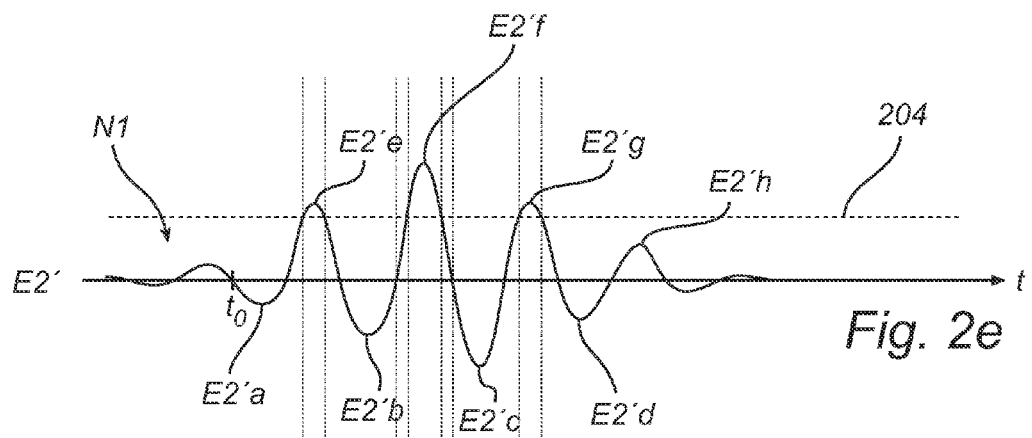
Fig. 2e
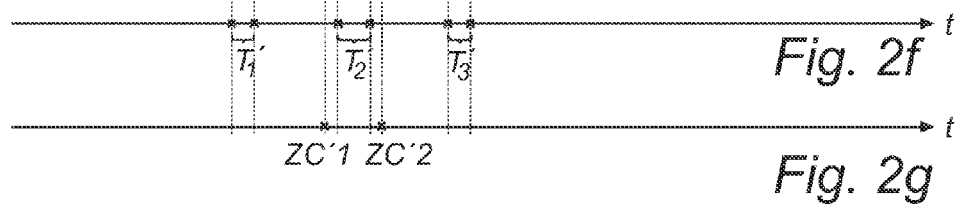
Fig. 2f
Fig. 2g

METHOD FOR DETERMINING THE STARTING INSTANT OF A PERIODICALLY OSCILLATING SIGNAL RESPONSE

TECHNICAL FIELD

The present invention relates to a method for determining the starting instant of a periodically oscillating signal response, a software for implementation thereof, and a device utilizing such a method.

BACKGROUND OF THE INVENTION

Acoustic measurement systems exist in several variants and may be used in many different areas, for example in measuring level or volume in tanks, containers or similar, in measuring distance, in measuring of flow, in medical diagnostics, such as ultrasound examination, in position determination etc.

An example is an echo type acoustic system for liquid level measurement. In such a system an acoustic transducer is typically provided at the highest point in a container which contains the liquid, the level or volume of which is to be measured. The acoustic transducer is fed from a transmitter with a first electric signal. In response to this first signal the transducer generates an acoustic pulse, typically in the form of an oscillating wave, which is transmitted downwards towards the surface of the liquid. After reflection against the surface the pulse is again picked up by the transducer which in response thereof generates a second electric signal which is fed to a receiver. The time interval between the first and the second electric signal, i.e. the transit time of the acoustic pulse, is determined and the distance from the transducer to the surface of the liquid can be calculated with a knowledge of the propagation velocity of the acoustic pulse in the medium in question.

Obviously in connection with such a transit time measurement it is important to be able to make an accurate determination of the time of reception of the reflected pulse or echo.

US 2007/0186624 discloses an acoustic method for measuring a signal propagation time in a medical liquid, where an oscillator-like received signal is sampled during its first half-period and checked with the help of a selection criterion based on the area enclosed between the resting level and the received signal during the half-period. When the result of this check is positive an intersection between the received signal and the resting level is determined with the help of which the signal transit time is calculated.

However, amplification or attenuation of the received signal typically changes as a function of temperature of the fluid in which acoustic signal propagates. This may cause erroneous measurements in applications where the temperature is not stable.

In an effort to reduce measurement errors caused by temperature changes, U.S. Pat. No. 6,226,598 discloses a method where an ideal characteristic first period is defined, which is characterized by an ideal amplitude ratio between the amplitudes of the two lobes of the ideal characteristic first period. Then, for each period of a received sound signal, the amplitudes of the two lobes of the period under examination are determined, and a ratio of the amplitudes is compared to the ideal amplitude ratio. If the result of the comparison is greater than a threshold value, the period under consideration is considered as being noise, whereas if the result of the comparison is less than the threshold value, the zero-crossing between the two lobes is considered to be the first zero-crossing of the received signal.

However, in some applications this method may be too computationally demanding.

SUMMARY OF THE INVENTION

In view of the above, an object of the invention is to substantially overcoming at least some of the disadvantages of the prior art. In particular, an object is to provide a computationally efficient method of determining the starting instant of a periodically oscillating signal response.

According to a first aspect of the invention, there is provided a method for determining the starting instant of a periodically oscillating signal response, wherein the signal response comprises a first set of half periods having a polarity equal to a polarity of the first half period in the signal response, and a second set of half periods having a polarity opposite to the polarity of the first half period in the signal response. The method comprises the steps of: determining a peak half period as the half period with the highest amplitude in a selected one of the first and second sets; determining a zero-crossing instant of the signal response occurring a known time distance from the peak half period; determining the starting instant of the signal response based on the zero-crossing instant and a relationship between the peak half period and the starting instant.

Note that the peak half period may be the half period that has the highest amplitude in the first set of half periods even if there is a half period with a higher amplitude in the second set. Similarly, it may be the half period that has the highest amplitude in the second set of half periods even if there is a half period with a higher amplitude in the first set. Thus, the peak half period is not necessarily the half period in the signal response that has the highest amplitude (although it may be).

By periodically oscillating here should be understood that the signal response is essentially periodic in its nature, although there may be a certain variation in the duration of the half periods. In particular, there may be a gradual shift within the signal response such that the first half period has a longer duration, whereas the duration of subsequent half periods are gradually reduced.

The present invention is based on the understanding that a reliable way to determine the starting instant of a periodically oscillating signal response is to find the peak half period (i.e. the half period of a given polarity having the highest amplitude) and then utilize a relationship between the peak half period and the starting instant of the signal response to determine the starting instant.

An advantage with this approach is that the half period having the highest amplitude in the selected set typically is easily detected (even if there is noise present). Thus, the method may be utilized with less sophisticated measurement equipment thereby enabling a cost-efficient solution.

The relationship between the peak half period and the starting instant of the signal response may be known in advance. For example, the nature of the signal response may be such that the half period having the highest amplitude is always the first half period in the second set. This allows a straight-forward and computationally efficient way to determine the starting instant.

The method may further comprise the steps of: determining a ratio between an amplitude of a preceding half period and an amplitude of the peak half period, wherein the preceding half period is the half period immediately preceding the peak half period in one of the first and second sets; comparing the ratio to a threshold value; and determining the number of half periods occurring between the peak half period and the starting instant of the signal response based on the comparison, thereby determining the relationship between the peak half period and the starting instant.

This enables an accurate measurement also in situations where the relationship between the peak half period and the starting instant is not known in advance, such as when the signal response has been distorted. An advantage is that since the method is less sensitive to distortion that may be caused by a change in Q-value of the transducer due to changes in temperature a low cost transducer can be utilized. This enables a more cost-efficient measuring device.

The threshold value may be selected so as to distinguish oscillations belonging to the signal response from oscillations being noise. The noise may be random noise, interference noise, or noise related to echoes arising from disturbances in the wave propagation.

When the ratio is below the threshold value, an interpretation may be that the peak half period is the half period in the selected set occurring immediately after the starting instant of the signal response. This enables the relationship between the peak half period and the starting instant to be established.

When the ratio is at least equal to (i.e. equal to or exceeds) the threshold value, an interpretation may be that there is at least one half period in the selected set occurring between the peak half period and the starting instant of the signal response.

According to an embodiment, the selected set is the second set of half periods. An advantage is that the amplitude of the half period having the highest amplitude in the second set typically is a larger than the amplitude of the half period having the highest amplitude in the first set. Thus, the peak half period is more easily detected and the measurement becomes less sensitive to noise.

According to an embodiment, the preceding half period belongs to the selected set. An advantage is that only one polarity needs to be detected, thereby enabling a more cost efficient measuring device.

The zero-crossing instant may preferably be the zero-crossing instant occurring immediately before or immediately after the peak half period, as detection of these are less sensitive to noise. However, it is recognized that other zero-crossing instants may also be utilized.

The peak half period and/or the ratio between the amplitudes (i.e. the ratio between the amplitude of the preceding half period and the amplitude of the peak half period) can be determined from a non-sampled representation of the signal response. As no sampling is required this enables a cost-efficient implementation and reduced power consumption. Furthermore, any inaccuracy that may be associated with the sampling procedure is eliminated.

The peak half period can be determined by: detecting a set of time periods during which the amplitude of the signal response exceeds a threshold amplitude and has a polarity equivalent to the polarity of the half periods in the selected set; and interpreting the longest time period in the set of time periods as corresponding to the peak half period. For a non-sampled representation of the signal response it may often be convenient to use the time during which the amplitude of a half period exceeds a given amplitude level as an indication of the amplitude rather than trying to directly measure the amplitude of the half period.

The method may further comprise the steps of: interpreting the time period which immediately precedes the longest time period in the set of time periods as corresponding to the preceding half period; and determining the ratio between the amplitude of the preceding half period and the amplitude of the peak half period based on the durations of the associated time periods.

An advantage is that these steps are applicable for a non-sampled representation of the signal response.

According to an embodiment, the peak half period may be determined by providing the signal response to a circuit comprising an energy storage medium; acquiring an output signal from said circuit, wherein said output signal corresponds to a voltage over the energy storage medium; sampling the acquired output signal; selecting a set of samples, wherein each sample in said set of samples is associated with a different one of the half periods in the selected one of the first and second sets of half periods and is detected at a predetermined occasion relative the associated half period; and determining the half period which is associated with the sample with the highest voltage as the peak half period.

As the circuit typically is configured such that the voltage reduction of the energy storage medium is slower than the voltage variation of the periodically oscillating signal response, the detected sample associated with a specific half period may be used as a direct indication of the amplitude of that half period. This enables a procedure that utilizes sampled data while minimizing the required processing of data and the memory capacity consumed, thereby allowing a low cost micro computer to be used. Furthermore, the less rapid voltage reduction means that a reliable result can be achieved also for a low cost A/D-converter.

The ratio between the amplitude of the preceding half period and the amplitude of the peak half period may be determined by providing the periodically oscillating signal response to a circuit comprising an energy storage medium; acquiring an output signal from said circuit, wherein the output signal corresponds to a voltage over said energy storage medium; sampling the acquired output signal; selecting a sample associated with the preceding half period and a sample associated with the peak half period; and determining the ratio between the amplitude of the preceding half period and the amplitude of the peak half period as the ratio between the voltage of the sample associated with the preceding half period and the voltage of the sample associated with the amplitude of the peak half period. The sample associated with the preceding half period may be detected at a predetermined occasion relative the preceding half period. Similarly, the sample associated with the peak half period may be detected at a corresponding predetermined occasion relative the peak half period. An advantage is that, due to a less rapid voltage reduction, a reliable result can be achieved also for a low cost A/D-converter.

The predetermined occasion relative the half period when the sample is detected may be determined by determining a zero-crossing instant that occurs at the end of the half period; and detecting a sample that occurs a predetermined time after the identified zero-crossing instant. For example, the next sample may be detected (i.e. the sample that occurs immediately after the zero-crossing).

A trigger signal used to generate the signal response may be configured such that for an ideal signal response, the half period with the largest amplitude appears as early as possible. Preferably the first half period in the second set of half periods is the half period with the largest amplitude.

An example of such a trigger signal would be a rectangular pulse having a duration of about one half period. Alternatively, a rectangular pulse having a duration of two half periods can be used. Such a trigger pulse may provide a signal response more suitable for detection according to the present invention. In particular, the signal response resulting from the second half period of the trigger signal will serve to suppress parts of the signal response resulting from the first half period of the trigger signal, thereby ensuring that the largest amplitude will appear early in the signal response.

It is recognized by a person skilled in the art that other types of trigger signals may also be used to generate a similar signal response. Thus, the shape of the pulse may vary. For example, a triangular pulse or a pulse having a rounded shape can be used. Furthermore the duration of the trigger signal may vary. Other examples of trigger signals would be an impulse, step, or a chirp.

According to a second aspect of the invention there is provided a software for execution on a processing device that has program instructions for implementation of the above described method.

According to a third aspect of the invention there is provided a device for acoustic measurement comprising: transducer means for transmitting and receiving a signal response; and a processing device arranged to perform the method according to the invention to determine the starting instant of the received signal response.

The acoustic measurement device may further comprise a circuit comprising an energy storing medium; and an analogue-to digital converter. An example of such a circuit would be a half-wave rectifier.

Other objectives, features and advantages will appear from the following detailed disclosure, from the attached dependent claims as well as from the drawings.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, where the same reference numerals will be used for similar elements, wherein:

FIG. 2a schematically illustrates the principle appearance of a trigger signal.

FIG. 2b-d schematically illustrates the principal appearance of a signal response, and associated time periods and zero-crossing instants registered by the control device.

FIG. 2e-g schematically illustrates the principal appearance of another signal response, and associated time periods and zero-crossing instants registered by the control device.

DETAILED DESCRIPTION OF PREFERRED EMBODIMENTS

Figure 1:
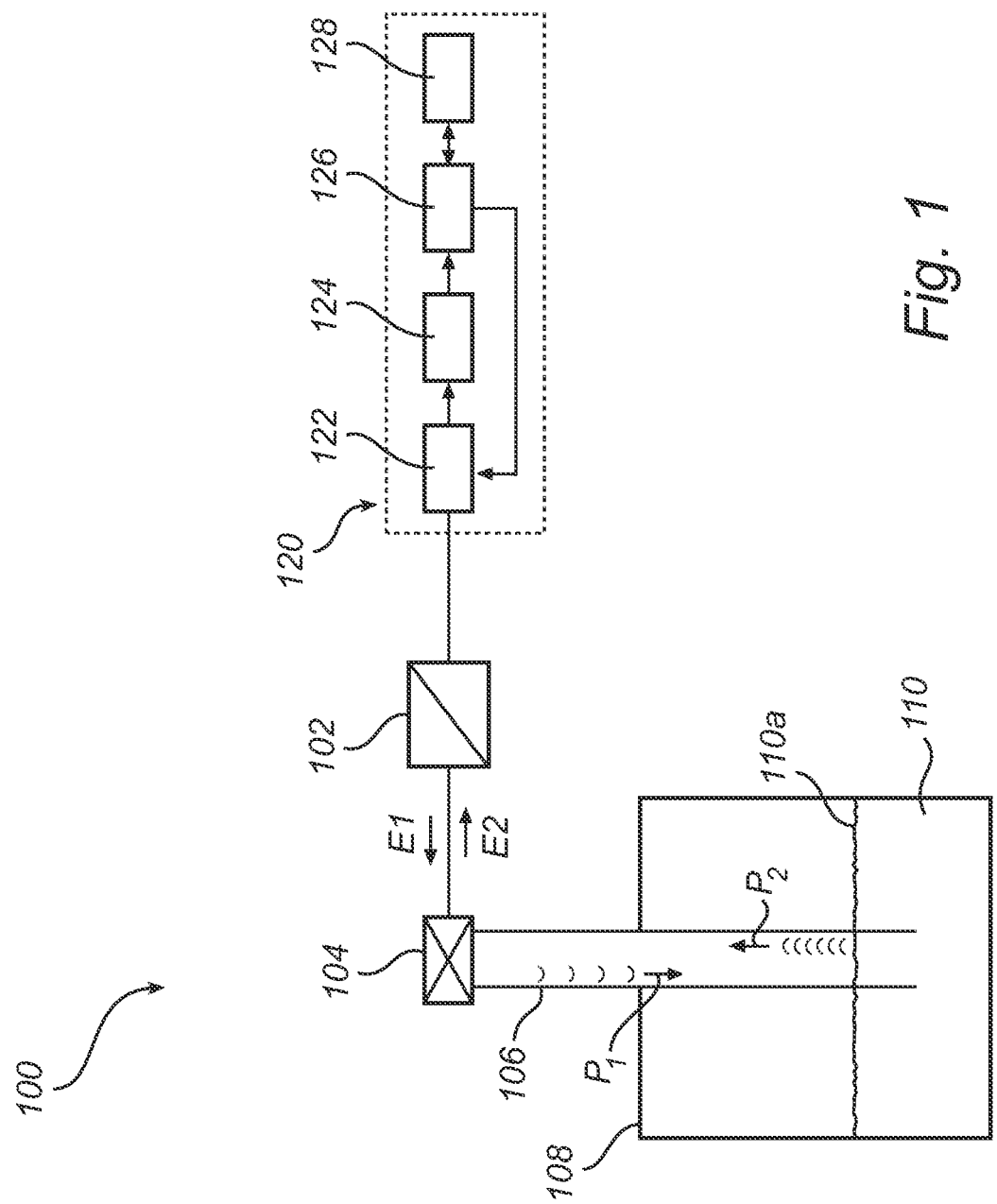
FIG. 1 is a schematic illustration of an acoustic level measuring system.

FIG. 1, shows schematically an acoustic level measuring system according to an embodiment of the invention. The system may typically operate below ultra-sound (i.e. below 20 kHz). However, the method according to the invention may also be applicable to systems operating at higher frequencies (i.e. ultra-sound frequencies).

The acoustic level measuring system 100 comprises a transmitter-receiver 102 which is electrically connected to an electro-acoustic transducer 104 disposed at the top of a tube 106. The transducer 104 may be constituted by a single unit, as shown in FIG. 1, or by a loudspeaker in combination with a microphone.

The tube 106 extends through the upper part of a container or tank 108 which contains a liquid 110, the level of which in the container is to be measured.

Furthermore, the transmitter-receiver 102 is connected to an electronic control device 120, which is arranged to control the transmitter-receiver 102 and to calculate the fluid level based on the signal transmitted and received by the transmitter-receiver 102.

In operation, the acoustic transducer 104 receives at predetermined intervals a first electric signal E1, also referred to as trigger signal E1, from the transmitter 102 and generates in response thereto an acoustic pulse P1, which is permitted to propagate through the tube 106 to be reflected against the liquid surface 110a, which is disposed above the lower edge of the tube 106. A certain time after the transmission, called the transit time of the pulse, the reflected pulse or echo P2 is received by the transducer 104, which transduces the echopulse P2 to a second electric signal E2 also referred to as signal response E2.

The electronic control device 120 receives the trigger signal E1, which causes the transmitted pulse P1, and also the response signal E2, which is generated at the reception of the reflected pulse P2 and determines the transit time of the pulse from the two electric signals E1 and E2 to evaluate the fluid level.

FIG. 2 schematically illustrates the principle appearance of the electric signals E1 and E2.

The trigger signal E1 received by the transducer is here a rectangular pulse with a duration of one half period and a negative polarity, whereas the resulting signal response E2 is a periodically oscillating signal having an essentially sinusoidal shape. The starting instant of the signal response E2 is indicated by $t_0$, and the first half period E2a in the signal response here has a negative polarity, i.e. the same polarity as the trigger signal E1. However, it is recognized that the polarity may be changed, for example, by switching the poles of the transducer.

As illustrated in FIG. 2b, the signal response E2 comprises a first set of half periods E2a-d having a negative polarity, and a second set of half periods E2e-h having a positive polarity. Furthermore, the signal response E2 is typically preceded by noise N1 here in the form of small oscillations.

The instants where the signal response E2 crosses the resting level 202 (i.e. when the amplitude of the signal response is zero relative the resting level) are referred to as zero-crossing instants ZC1-ZC2. The resting level is here assumed to be at 0V although it may also be offset by a DC-voltage.

Unless the signal response E2 is somehow distorted (which will be further discussed below in relation to FIG. 2e), the rectangular pulse E1 will cause a signal response E2 where the first positive half period E2e is the positive half period in the signal response that has the highest amplitude, whereas the amplitude of subsequent positive half periods E2f-h will attenuate quickly, thereby creating a signal response having a distinct amplitude peak near the beginning of the signal response. This undistorted signal is an example of an ideal signal response.

In order to accurately determine the transit time of the pulse the electronic control device 120 typically utilizes the starting instant of the trigger signal E1 and the starting instant of the signal response E2.

As is recognized by a person skilled in the art, determining the starting instant of the trigger signal E1 is straight-forward and thus will not be further discussed herein.

In order to determine the starting instant $t_0$ of the signal response E2, the electronic control device 120 comprises an amplifier 122, a comparator 124, and a processing device 126 with an associated memory 128.

The comparator 124 is configured to detect when the amplitude of the signal response E2 exceeds an amplitude threshold.

Here the comparator only detects when the amplitude of the signal response E2 exceeds a positive amplitude threshold (i.e. the negative half periods E2*a-d* will not be evaluated here, although such an embodiment would be possible). It is recognized by a person skilled in the art that the level of the amplitude threshold may vary depending on the application. However, a typical value of the amplitude threshold may be about 50% of the saturation voltage of the comparator.

The amplitude threshold 204 of the comparator 124 is shown in relation to the signal response E2 in FIG. 2*b*. Here the first positive half period E2*e* and the second positive half period E2*f* of the signal response exceeds the amplitude threshold 204 of the comparator, whereas subsequent half periods E2*g-h* are below the amplitude threshold 204. Also the noise N1 is below the amplitude threshold 204 in the illustrated example.

The amplitude of the signal response E2 can be adapted by adjusting the amplification of the amplifier 122 arranged between the receiver 102 and the comparator 124. Thus, it is possible to e.g. reduce the amplification so that only one (or none) of the positive half periods exceeds the amplitude threshold or increase the amplification so that more than two positive half periods exceed the amplitude threshold.

The comparator 124 is connected to the processing device 126, which registers when a received signal has an amplitude exceeding the amplitude threshold 204. This information can then be stored in the memory 128.

The processing device 126 also has functionality to register when the received signal crosses the resting level 202, and store this information in the memory 128.

In operation, as a signal response E2 is received by the receiver 102, the electronic control device 120 registers a set of time periods representing the intervals during which the amplitude of the received signal E2 exceeds the positive amplitude threshold 204.

For the measurement situation shown in FIG. 2*b*, two time periods $T_1$ and $T_2$ are registered by the control device as illustrated in FIG. 2*c*. Here the time period $T_1$ indicates the occurrence of half period E2*e*, and the time period $T_2$ indicates the occurrence of half period E2*f*.

Furthermore, the electronic control device 120 registers a set of zero-crossing instants ZC1-ZC2 for the signal response E2 as illustrated in FIG. 2*d*.

Figure 3:
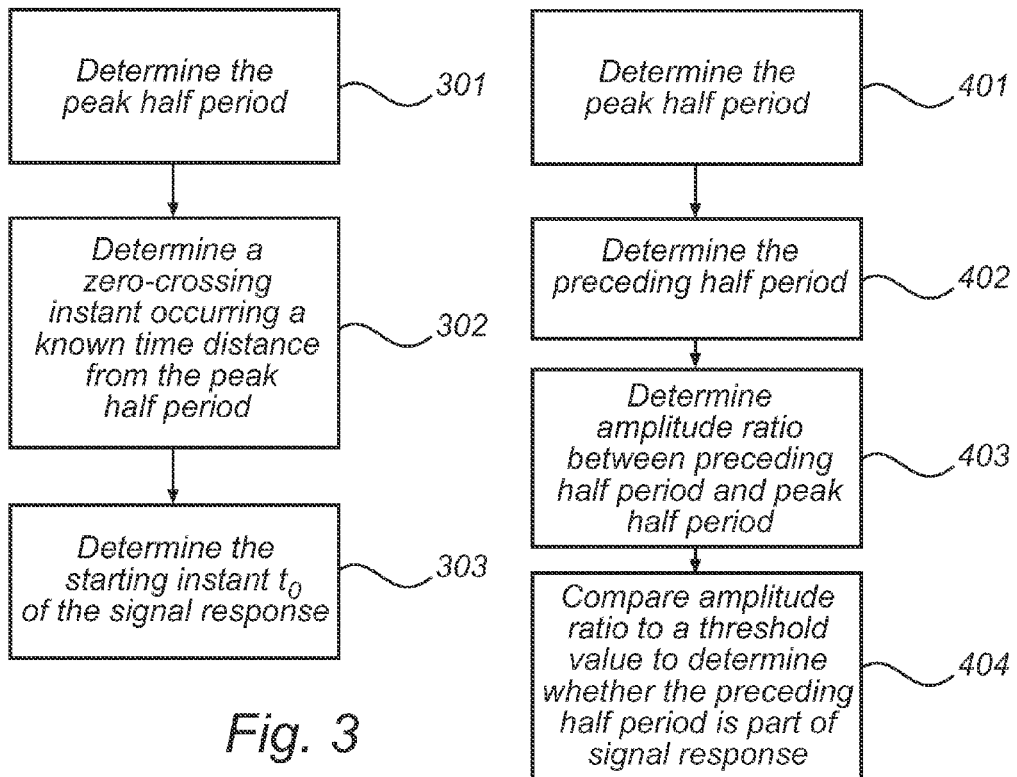
FIG. 3 is a schematic block diagram illustrating a procedure for determining the starting instant of a periodically oscillating signal response.

A method for determining the starting instant of the signal response E2 will now be described with reference to FIG. 2 and to the schematic block diagram illustrated in FIG. 3.

Note that it is here assumed that the positive half period having the highest amplitude in the signal response E2 is the first positive half period E2*e*.

First in step 301, a peak half period is determined as the positive half period having the highest amplitude. The longest time period $T_1$ registered by the control device 120 is here interpreted as an indication of the positive half period E2*e* having the highest amplitude.

It can be noted that in some situation it may be convenient to adjust the amplification of the amplifier 122 in a way that only the positive half period having the highest amplitude exceeds the amplitude threshold 204 to facilitate identification of the peak half period.

Then in step 302, a zero-crossing instant of the signal response occurring a known time distance from the peak half period E2*e* is determined. It may be preferable to utilize the zero-crossing instant occurring immediately before or immediately after the peak half period E2*e*. However, other zero-crossing instants may also be used. Here, the zero-crossing instant ZC1 occurring immediately before the peak half period E2*e* is used.

In step 303, the starting instant $t_0$ of the signal response E2 is then determined based on the zero-crossing instant ZC1 and a relationship between the peak half period E2*e* and the starting instant $t_0$ of the signal response. As it has here been assumed that the positive half period having the highest amplitude in the signal response is the first positive half period E2*e*, the peak half period E2*e* is here per definition the first positive half period in the signal response. As the signal response E2 starts with a negative half period, it is known that there will be one half period occurring between the peak half period E2*e* and the starting instant $t_0$ (i.e. the first negative half period E2*a*). Furthermore, as the zero-crossing instant ZC1 has been selected as the zero-crossing instant occurring immediately before the peak half period E2*e*, it can be concluded that the starting instant $t_0$ of the signal response occurs one half period before the zero-crossing instant ZC1.

Assuming that the signal response is essentially sinusoidal the starting instant can be calculated as:

$$t_0 = t_{ZC1} - \frac{T}{2},$$

where $t_0$ is the starting instant of the signal response;

$t_{ZC1}$ is the time of occurrence of the zero-crossing instant ZC1; and T is the time for one period of the oscillating signal response.

Although the above described method is applicable in a wide range of situations, there are situations where it may not be assumed that the positive half period having the highest amplitude in the signal response is the first positive half period.

For example, there are situations where the signal response E2 may be distorted so that the peak half period no longer is the first positive half period. This is illustrated by the distorted signal response E2' in FIG. 2*e* where the positive half period having the highest amplitude is the second positive half period E2'*f*.

Such a distortion may be caused for example by a change in Q-value of the transducer 104. The Q-value of the transducer may vary as a function of temperature, especially for a low cost transducer. Thus, a distortion of the signal response may arise in applications where the temperature is not stable.

It is recognized that if it is not known whether the peak half period is the first or second positive half period in the signal response this may lead to a measurement error of one period thereby significantly decreasing the measurement accuracy of the acoustic level measuring system.

In order to overcome this problem, the number of half periods occurring between the peak half period E2'f and the starting instant $t_0$ of the signal response E2' can be determined.

To do this a ratio between an amplitude of the positive half period E2'e immediately preceding the peak half period and an amplitude of the peak half period E2'f is compared to a threshold value selected so as to distinguish oscillations belonging to the signal response from oscillations being noise.

In a typical application the threshold value may be about 40%. However, the preferred threshold value may vary based on the magnitude of the noise and on the magnitude of the distortion of the signal response.

For example, in applications where the expected distortion of the signal response is low, the threshold value can be set as high as 80% to reduce the risk that any noise is interpreted as being part of the signal response. A high threshold value may also be preferred if there is a lot of noise present.

On the other hand, under favourable conditions with little noise present the threshold value may be set as low as 15% or even 10%. A low threshold value enables a low-cost transducer (with a less stable Q-value) to be used, thereby enabling a more cost-efficient measurement device.

In some applications it may be convenient to determine the number of half periods occurring between the peak half period E2'f and the starting instant $t_0$ of the signal response E2' by selecting the amplitude threshold 204 of the comparator 124 so that it coincides with the threshold value. Thus, if there is a time period registered by the comparator 124 which occurs before the time period associated with the peak half period this time period will be the first positive half period.

A method for determining the starting instant of the signal response E2' will now be described with reference to FIG. 2e-g and to the schematic block diagram illustrated in FIG. 4.

In this embodiment it is assumed that the amplitude threshold 204 of the comparator 124 is set so as to coincide with the threshold value. It is also assumed that the peak half period is the first or second positive half period in the signal response.

First in step 401, a peak half period is determined as the positive half period having the highest amplitude. The longest time period $T'_2$ registered by the control device 120 is here interpreted as an indication of the positive half period E2'f having the highest amplitude.

Then in step 402, the preceding half period is determined as the positive half period immediately preceding the peak half period E2'f. The time period $T'_1$ which immediately precedes the longest time period $T'_2$ is thus interpreted as an indication of the positive half period E2'e immediately preceding the peak half period E2'f.

In step 403 a ratio between an amplitude of the preceding half period and an amplitude of the peak half period is determined, and then in step 404 this amplitude ratio is compared to a threshold value. However, in this embodiment step 403 and 404 is not explicitly performed. As the amplitude threshold 204 of the comparator 124 is set so as to coincide with the threshold value, the mere existence of the time period $T'_1$ indicates that the preceding half period belongs to the signal response (whereas if no time period would be detected before the time period $T'_2$ this would indicate that the peak half period would be the first positive half period in the signal response).

In step 405, a zero-crossing instant of the signal response occurring a known time distance from the peak half period E2'f is determined. Here, the zero-crossing instant ZC'1 occurring immediately before the peak half period E2'f is used.

In step 406, the starting instant $t_0$ of the signal response E2' is then determined based on the zero-crossing instant ZC'1 and a relationship between the peak half period E2'f and the starting instant $t_0$. As it has been determined in step 402 that that there is one positive half period (i.e. positive half period E2'e) occurring between peak half period E2'f and the starting instant $t_0$, it is known that there are three half periods (i.e. E2'a, E2'b and E2'e) occurring between the peak half period E2'f and the starting instant $t_0$. Furthermore, as the zero-crossing instant has been selected as the zero-crossing instant ZC'1 occurring immediately before the peak half period E2'f, it can be concluded that the starting instant $t_0$ of the signal response occurs three half periods before the zero-crossing instant ZC'1.

Assuming that the signal response is essentially sinusoidal the starting instant can be calculated as:

$$t_0 = t_{ZC'1} - 3 \cdot \frac{T}{2},$$

where
$t_0$ is the starting instant of the signal response;
$t_{ZC'1}$ is the time of occurrence of the zero-crossing instant ZC'1; and
T is the time for one period of the oscillating signal response.

In some applications there may be a variation in the duration of the half periods in the signal response (i.e. the time T is not constant throughout the signal response). It is recognized by a person skilled in the art that it is possible to compensate for such a variation.

Naturally the method also works for a signal response where the peak half period is the first positive half period. This can be understood by looking at the signal response E2 illustrated in FIG. 2b. In this case there will be no time period registered before the longest time period $T_1$ which is associated with the peak half period E2e. Thus it is known that the peak half period E2e is the first positive half period. The starting instant can then be determined by finding the zero-crossing instant ZC1 immediately before the peak half period E2e. The starting instant $t_0$ of the signal response E2 will occur one half period before the zero-crossing instant ZC1.

According to an alternative embodiment, the amplitude threshold of the comparator is lower than the threshold value, wherein step 403 and 404 can be explicitly performed as described below with reference to FIG. 2e-g and FIG. 4.

In step 403, the ratio between the amplitude $A_{prec}$ of the preceding half period E2'e and the amplitude $A_{peak}$ of the peak half period E2'f is determined based on the durations of the associated time periods.

Assuming that the signal response E2' is essentially sinusoidal, the amplitudes of the respective half period can be calculated by basic trigonometry.

In step 404, the ratio is then compared to the threshold value to determine whether the preceding half period is part of the signal response, or should be considered to be noise. If the ratio exceeds the threshold value, i.e.

$$\frac{A_{prec}}{A_{peak}} \geq \text{threshold},$$

the preceding half period is considered to belong to the signal response, if not the preceding half period is considered to be noise.

Figure 5:
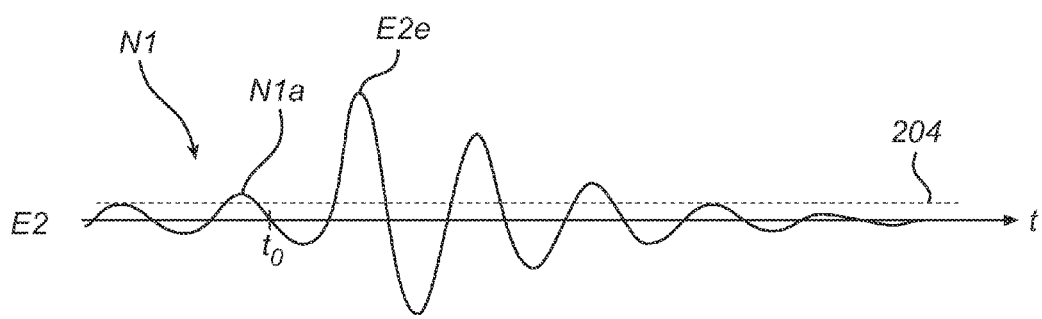
FIG. 5 illustrates another signal response.

FIG. 5 illustrates a situation where the threshold amplitude 204 is sufficiently low for noise N1 to be registered by the comparator. In such a situation a ratio is determined between an amplitude of a preceding half period N1a (resulting from noise) and an amplitude of the peak half period E2e. However, as the ratio is here below the threshold value, the preceding half period N1a will here be considered not to be part of the signal response, and the peak half period E2e will be considered to be the first positive half period in the signal response.

The method according to the invention is also applicable when the peak half period is preceded by more than one positive half period by finding the peak half period and then iteratively evaluating how many positive half periods that are situated between the peak half period and the starting instant.

Figure 6:
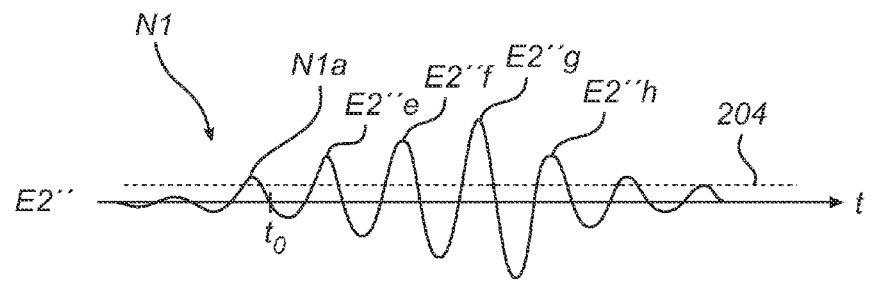
FIG. 6 illustrates yet another signal response.

An example thereof will now be described with reference to FIG. 6. Here two positive half periods E2"e-f are situated between the peak half E2"g and the starting instant $t_0$.

First, the peak half period E2"g is determined. Then the ratio between the amplitude of the preceding half period E21 and the peak half period E2"g is determined. As this ratio exceeds the threshold value, the preceding half E2"f is interpreted as a half period occurring between the peak half period and the starting instant $t_0$. Next a ratio between an amplitude of a new preceding half period (here the positive half period E2"e immediately preceding the most recently identified half period E2"f) and an amplitude of the most recently identified half period E2"f is determined. As the ratio between the amplitude of the new preceding half period E2"e and the most recently identified half period E21 exceeds the threshold value the new preceding half period E2"e is interpreted as a half period occurring between the peak half period E2"g and the starting instant $t_0$. In the next iteration a ratio between the amplitude of the half period N1a being noise and the amplitude of the most recently identified half period E2"e is determined. As this ratio is below the threshold value, the half period N1a will be disregarded and the half period E2"e will be considered as the first positive half period in the signal response. This also means that the iteration stops.

In embodiments where an amplitude ratio is calculated, the amplitude threshold 204 of the comparator preferably is selected so as to achieve a good indication of the amplitude of the evaluated half periods.

If the amplitude threshold is set too high (relative the amplitude of the evaluated half periods), there is a risk that the first positive half period in the signal response is not detected by the comparator. On the other hand, if the amplitude threshold is set too low (relative the amplitude of the evaluated half periods), a small change in time registered by the comparator will correspond to a relatively large change in amplitude of the signal response (as the derivative of the signal response is large close to the resting level and successively gets smaller until it is about zero near the top of the half period).

To find an appropriate amplitude threshold a calibration procedure can be performed when measuring is started and/or when the signal is lost. An example thereof as is described below with reference to FIG. 1 and FIG. 2b.

As the calibration procedure is initiated the amplification of the amplifier 122 is low. A series of essentially identical trigger signals E1 are then generated. For each trigger signal E1 a corresponding received signal response E2 is registered by the processing device 126. The processing device 126 controls the amplifier 122 by means of a feedback loop, and increases the amplification for each received signal response E2 until the amplitude of the positive half period having the highest amplitude (here the peak amplitude E2e) saturates the comparator 124. In a typical application the saturation voltage of the comparator 124 may be about 5V.

The amplitude threshold 204 is then set to about 50% of the saturation voltage of the comparator, i.e. here about 2.5V.

Figure 7:
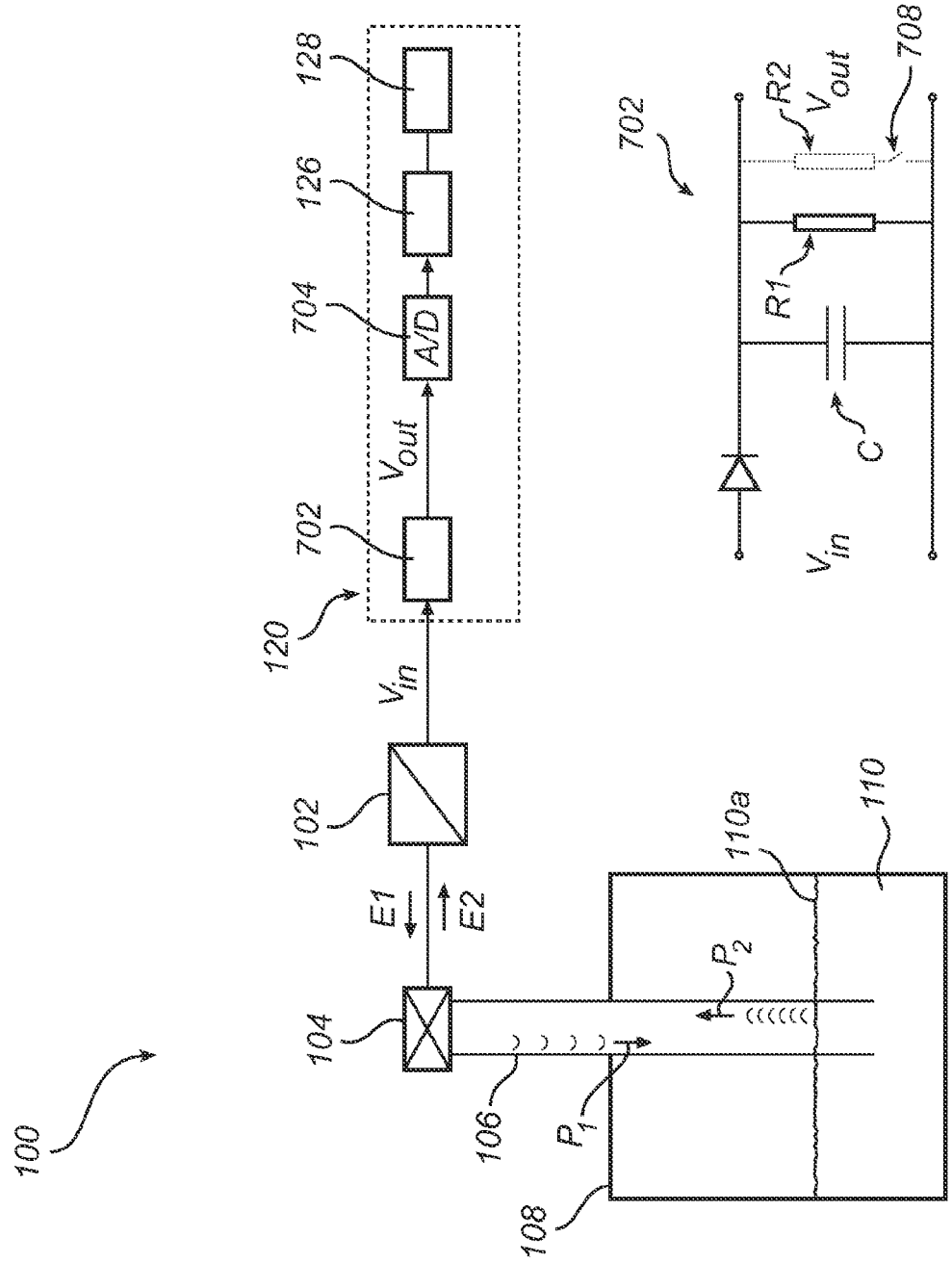
FIG. 7a schematically illustrates an alternative embodiment of the invention where the control device comprises a half-wave rectifier and an ND-converter.
FIG. 7b schematically illustrates an example of a half-wave rectifier.

FIG. 7a schematically illustrates an alternative embodiment of the invention. This embodiment differs from the previously described embodiments in that the electronic control device 120 comprises a circuit 702 comprising an energy storage medium C, and an analogue-to-digital (ND) converter 704 for sampling a signal acquired from the circuit 702. As schematically illustrated in FIG. 7b, the circuit 702 may be a half-wave rectifier 702 comprising a diode 706, a resistor R1, and the energy storage medium C which is here a capacitor C.

The operation of the electronic control device 120 will now be described with reference to FIG. 7a-b and FIG. 8. Here the input voltage $V_{in}$ applied to the half-wave rectifier 702 is the signal response E2'. Further, it is here assumed that the capacitor C initially is discharged.

Figure 8:
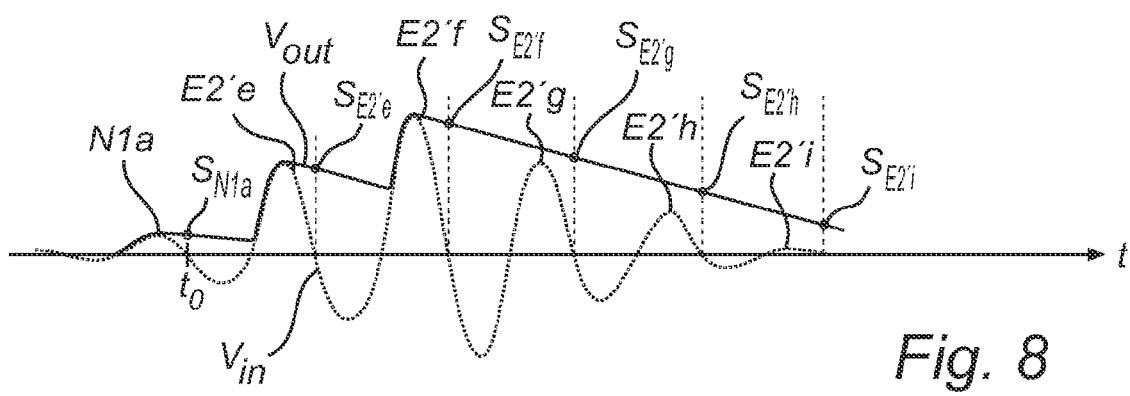
FIG. 8 schematically illustrates an input signal supplied to the half-wave rectifier and a resulting output signal.

FIG. 8 schematically illustrates the input voltage $V_{in}$ applied to the half-wave rectifier 702 and the corresponding output voltage $V_{out}$ (which is here the voltage over the capacitor C) output by the half-wave rectifier 702 as a function of time.

As the first positive half period N1a (here being noise) is received by the half-wave rectifier 702, the input voltage $\f_{in}$ applied to the half-wave rectifier 702 is gradually increased, resulting in a corresponding increase in the output voltage $V_{out}$ of the half-wave rectifier 702. The input voltage $V_{in}$ also charges the capacitor C. Then, as the input voltage $V_{in}$ is reduced (i.e. after the peak of the first positive half period N1a) the capacitor C starts to discharge, and the output voltage $V_{out}$ of the half-wave rectifier 702 is reduced. However, as appears from FIG. 8, the voltage reduction of the signal $V_{out}$ output by the circuit 702 is substantially slower than the voltage reduction of the signal response E2'.

Then, as the second positive half period E2'e is received by the half-wave rectifier 702, the input voltage $V_{in}$ is again gradually increased and as the input voltage $V_{in}$ exceeds the voltage over the capacitor C, the capacitor starts charging again. Then, as the input voltage $V_{in}$ is reduced (i.e. after the peak of the second positive half period E2'e) the capacitor C once again starts to discharge and the output voltage $V_{out}$ again is reduced.

This procedure is then repeated for the subsequent positive half periods E2'f-i.

The ND-converter 704 may typically be adapted to continuously sample the signal $V_{out}$ output by the half-wave rectifier at a predetermined sampling frequency.

In order to determine the amplitude of each positive half period E2'e-i, the control device 120 may be configured to select a set of samples, wherein each sample ($S_{N1a}$, $S_{E2'e-i}$) is associated with a different one of the half period (N1a, E2'e-i), and selected such that each of the selected samples is detected at a predetermined occasion relative the half period in question. For example, the zero-crossing instant at the end of the half period can be used to trigger the control device 120 to store the next sample acquired from the A/D-converter 704 in a memory 128. In the illustrated example, this results in samples, $S_{N1'a}$, $S_{E2'e}$ $S_{E2'f}$ $S_{E2'g}$, $S_{E2'h}$, and $S_{E2'i}$ as indicated in FIG. 8. The peak half period E2'f can then be found as the positive half period associated with the sample with the largest amplitude, i.e. here the positive half period E2'f is the peak half period.

Note that, although the voltage of samples $S_{E2'g}$, $S_{E2'h}$, and $S_{E2'i}$ are here higher than the voltage of the corresponding half periods E2'g-i of the signal response, an accurate result is achieved, since it suffice to determine that these subsequent half periods E2'g-i are lower than the previous half period E2'f.

Figure 4:
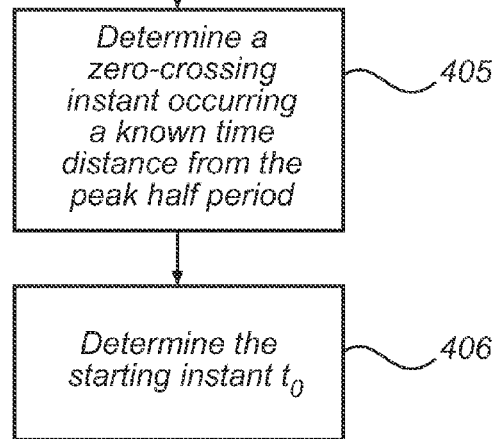
FIG. 4 is a schematic block diagram illustrating another procedure for determining the starting instant of a periodically oscillating signal response.

After the peak half period E2'f has been determined, the starting instant $t_0$ of the periodically oscillating signal E2' can be determined according to the procedure illustrated in FIG. 4. In doing so, the voltage of the samples can be used to calculate the amplitude ratio. For example, the ratio between the amplitude of the preceding half period E2'e and the amplitude of the peak half period E2'f can be determined as the ratio between the voltage of the sample $S_{E2'e}$ associated with preceding half period E2'e and the voltage of the sample $S_{E2'f}$ associated with the amplitude of the peak half period E2'f.

As is recognized by a person skilled in the art the rate of discharge of the capacitor C, and thus the rate at which the output voltage $V_{out}$ of the half-wave rectifier is reduced can be adjusted by changing the resistance of the resistor R1 and/or the capacitance of the capacitor C. Since the output voltage $V_{out}$ is used to compare different half periods or to calculate a ratio between different half periods, the rate at which the output voltage is reduced is typically not critical for the reliability of the procedure. Thus, the rate at which the output voltage is reduced may preferably be selected to be sufficiently rapid for a subsequent echo to be detected. Alternatively, the circuit may comprise another (optional) resistor R2 that can be connected in parallel with the resistor R1. Thus, by closing a switch 708 after an echo has been detected the half-wave rectifier may be reset. The invention has mainly been described above with reference to a few embodiments. However, as is readily appreciated by a person skilled in the art, other embodiments than the ones disclosed above are equally possible within the scope of the invention, as defined by the appended claims.

For example, although the above described comparator only detects half periods having a positive polarity it would be possible to have an arrangement where the comparator detects only half periods having negative polarity, or a comparator which detects half periods of both polarities.

Furthermore, in a situation where half periods of both polarities are detected, a ratio between amplitudes of half periods having opposite polarities may be determined and compared to a threshold value. For example, referring to FIG. 2e, a ratio between the amplitude of half period E2'f and the amplitude of half period E2'b may be determined and compared to a threshold value when determining the number of half periods situated between the peak half period and the starting instant $t_0$.

Also a ratio between amplitudes of two negative half periods can be determined and compared to a threshold value when determining the number of half periods situated between the peak half period and the starting instant $t_0$.

Furthermore, for embodiments where sampling is used, it may be possible to sample the signal response directly if the ND-converter has a sufficiently high sampling frequency (i.e. the circuit with the energy storage medium may be omitted).

It is recognized that although the illustrated example shows a wave-package propagating in a wave-guide, the invention is equally applicable to a wave-package propagating in free air.

The invention claimed is:

1. A method for determining the starting instant of a periodically oscillating signal response, wherein said signal response comprises a first set of half periods having a polarity equal to a polarity of the first half period in the signal response, and a second set of half periods having a polarity opposite to the polarity of the first half period in the signal response, said method comprising:

determining, using an electronic control device, a peak half period as the half period with the highest amplitude in a selected one of said first and second sets;

determining, using the electronic control device, a zero-crossing instant of said signal response occurring a known time distance from said peak half period;

determining the starting instant of said signal response based on said zero-crossing instant and a relationship between said peak half period and said starting instant;

wherein determining the relationship between said peak half period and said starting instant comprises:

determining a ratio between an amplitude of a preceding half period and an amplitude of said peak half period, wherein said preceding half period is the half period immediately preceding said peak half period in one of said first and second sets;

comparing said ratio to a threshold value; and determining the number of half periods occurring between said peak half period and the starting instant of the signal response based on said comparison.

2. A method according to claim 1, further comprising:
when said ratio is below said threshold value, interpreting that said peak half period is the half period in said selected set occurring immediately after said starting instant of the signal response.

3. A method according to claim 1, further comprising:
when said ratio is at least equal to said threshold value, interpreting that there is at least one half period in said selected set occurring between said peak half period and the starting instant of the signal response.

4. A method according to claim 3, further comprising:
interpreting that there is only one half period in said selected set occurring between said peak half period and the starting instant of the signal response.

5. A method according to claim 1, wherein said selected set is said second set of half periods.

6. A method according to claim 1, wherein said preceding half period belongs to said selected set.

7. A method according to claim 1, wherein the zero-crossing instant is the zero-crossing instant occurring immediately before or immediately after the peak half period.

8. A method according to claim 1, wherein said threshold value is selected so as to distinguish oscillations belonging to the signal response from oscillations being noise.

9. A method according to claim 1, wherein the peak half period is determined by:

providing said signal response to a circuit comprising an energy storage medium;

acquiring an output signal from said circuit, wherein said output signal corresponds to a voltage over said energy storage medium;

sampling the acquired output signal;

selecting a set of samples, wherein each sample in said set of samples is associated with a different one of the half periods in the selected one of said first and second sets of half periods and is detected at a predetermined occasion relative the associated half period; and determining the half period which is associated with the sample with the highest voltage as said peak half period.

10. A method according to claim 1, wherein the ratio between the amplitude of said preceding half period and the amplitude of said peak half period is determined by:

providing said signal response to a circuit comprising an energy storage medium;

acquiring an output signal from said circuit, wherein said output signal corresponds to a voltage over said energy storage medium;

sampling the acquired output signal;

selecting a sample associated with said preceding half period and a sample associated with said peak half period; and determining the ratio between the amplitude of the preceding half period and the amplitude of said peak half period as the ratio between the voltage of the sample associated with said preceding half period and the voltage of the sample associated with the amplitude of said peak half period.

11. A method according to claim 9, wherein the predetermined occasion relative the half period when the sample is detected is determined by: determining a zero-crossing instant that occurs at the end of the half period; and selecting a sample that occurs a predetermined time after the identified zero-crossing instant.

12. A method according to claim 1, wherein a trigger signal used to generate the signal response is configured such that for an ideal signal response the first half period in the second set of half periods is the half period with the highest amplitude.

13. A method according to claim 1, wherein at least one of the peak half period and the ratio between the amplitudes is determined from a non-sampled representation of said signal response.

14. A method according to claim 13, wherein the peak half period is determined by:

detecting a set of time periods during which the amplitude of the signal response exceeds a threshold amplitude and has a polarity equivalent to the polarity of the half periods in the selected set interpreting the longest time period in said set of time periods as corresponding to said peak half period.

15. A method according to claim 14, further comprising:

interpreting the time period which immediately precedes the longest time period in said set of time periods as corresponding to said preceding half period; and determining the ratio between the amplitude of said preceding half period and the amplitude of said peak half period based on the durations of the associated time periods.

16. A device for acoustic measurement comprising:

a transducer means for transmitting and receiving a signal response; and the electronic control device arranged to perform the method of claim 1 to determine the starting instant of the received signal response.

* * * * *